(12) United States Patent
Shallom (10) Patent No.: US 12,207,903 B2
(45) Date of Patent: *Jan. 28, 2025

(54) DIAGNOSIS OF MEDICAL CONDITIONS USING VOICE RECORDINGS AND AUSCULTATION

(71) Applicant: CORDIO MEDICAL LTD., Or-Yehuda (IL)

(72) Inventor: Ilan D. Shallom, Gedera (IL)

( * ) Notice: Subject to any disclaimer, the term of this patent is extended or adjusted under 35 U.S.C. 154(b) by 72 days.

This patent is subject to a terminal disclaimer.

(21) Appl. No.: 17/902,836

(22) Filed: Sep. 4, 2022

(65) Prior Publication Data

US 2022/0409063 A1    Dec. 29, 2022

Related U.S. Application Data

(63) Continuation of application No. 16/807,178, filed on Mar. 3, 2020, now Pat. No. 11,484,211.

(51) Int. Cl.
*A61B 5/02* (2006.01)
*A61B 5/00* (2006.01)
(Continued)

(52) U.S. Cl.
CPC .......... *A61B 5/0205* (2013.01); *A61B 5/4836* (2013.01); *A61B 5/4878* (2013.01);
(Continued)

(58) Field of Classification Search
CPC ... A61B 5/0205; A61B 5/4836; A61B 5/4878; A61B 5/7203; A61B 5/725; A61B 5/7282; A61B 5/4803; A61B 7/04; A61B 2560/0475; A61B 7/003; A61B 7/026; G10L 25/66; G16H 50/20

See application file for complete search history.

(56) References Cited

U.S. PATENT DOCUMENTS

| 6,168,568 | B1 * | 1/2001 | Gavriely | A61B 5/087 |
| | | | | 600/529 |
| 10,311,980 | B2 | 6/2019 | Kim et al. | |

(Continued)

FOREIGN PATENT DOCUMENTS

| DE | 102015218948 A1 | 3/2017 |
| JP | 2003044078 A | 2/2003 |

(Continued)

OTHER PUBLICATIONS

IN Application # 202247044184 Office Action dated Nov. 9, 2022.
(Continued)

*Primary Examiner* — Rex R Holmes
(74) *Attorney, Agent, or Firm* — Meitar Patents Ltd.; Daniel Kligler (57) ABSTRACT

A method for medical diagnosis includes recording voice signals due to sounds spoken by a patient and recording acoustic signals output, simultaneously with the voice signals, by an acoustic transducer in contact with a thorax of the patient. A transfer function is computed between the recorded voice signals and the recorded acoustic signals or between the recorded acoustic signals and the recorded voice signals. The computed transfer function is evaluated in order to assess a medical condition of the patient.

35 Claims, 3 Drawing Sheets

(51) Int. Cl.
  *A61B 5/0205* (2006.01)
  *G10L 25/66* (2013.01)
  *G16H 50/20* (2018.01)
  *A61B 7/04* (2006.01)

(52) U.S. Cl.
  CPC ............ *A61B 5/7203* (2013.01); *A61B 5/725* (2013.01); *A61B 5/7282* (2013.01); *G10L 25/66* (2013.01); *G16H 50/20* (2018.01); *A61B 5/4803* (2013.01); *A61B 7/04* (2013.01); *A61B 2560/0475* (2013.01)

(56) References Cited

U.S. PATENT DOCUMENTS

| | | | |
|---|---|---|---|
| 10,896,765 | B2 | 1/2021 | Kim et al. |
| 10,991,384 | B2 | 4/2021 | Eyben et al. |
| 2017/0262606 | A1 | 9/2017 | Abdullah et al. |
| 2018/0214061 | A1 | 8/2018 | Knoth et al. |
| 2019/0385711 | A1 | 12/2019 | Shriberg et al. |
| 2020/0098384 | A1 | 3/2020 | Nematihosseinabadi et al. |
| 2021/0110894 | A1 | 4/2021 | Shriberg et al. |
| 2021/0193169 | A1 | 6/2021 | Faizakof et al. |
| 2022/0130415 | A1 | 4/2022 | Garrison et al. |
| 2022/0328064 | A1 | 10/2022 | Shriberg et al. |
| 2022/0415308 | A1 | 12/2022 | Berisha et al. |
| 2023/0072242 | A1 | 3/2023 | Kim et al. |

FOREIGN PATENT DOCUMENTS

| | | | |
|---|---|---|---|
| JP | 2004302786 | A | 10/2004 |
| JP | 2006230548 | A | 9/2006 |
| JP | 2016006504 | A | 1/2016 |
| JP | 2017191166 | A | 10/2017 |
| JP | 6263308 | B1 | 1/2018 |
| WO | 2005074799 | A1 | 8/2005 |
| WO | 2006033044 | A3 | 3/2006 |
| WO | 2019089830 | A1 | 5/2019 |

OTHER PUBLICATIONS

U.S. Appl. No. 17/233,487 Office Action dated Dec. 29, 2022.
CN Application # 2020800180012 Office Action dated Jan. 30, 2024.
IN Application # 202347030550 Office Action dated Dec. 13, 2023.
CN Application # 2019800670875 Office Action dated Dec. 20, 2023.
JP Application # 2021549583 Office Action dated Dec. 25, 2023.
JP Application # 2021551893 Office Action dated Dec. 25, 2023.
CN Application # 202080017839X Office Action dated Jan. 27, 2024.
AU Application # 2021229663 Office Action dated Aug. 10, 2023.
EP Application # 20158058.6 Summons to Oral Proceedings dated Apr. 19, 2023.
EP Application # 19201720.0 Office Action dated Mar. 30, 2023.
EP Application # 21209891.7 Office Action dated May 19, 2023.
JP Application # 2021-517971 Office Action dated May 16, 2023.
Indian Application # 202247066856 Office Action dated Mar. 29, 2023.
Sakran et al., "A Review: Automatic Speech Segmentation", International Journal of Computer Science and Mobile Computing (IJCSMC), vol. 6, issue 4, pp. 308-315, Apr. 2017.
Nicora et al., "Evaluating pointwise reliability of machine learning prediction", Journal of Biomedical Informatics, vol. 127, pp. 1-15, Mar. 2022.
Haimi-Cohen et al., U.S. Appl. No. 18/328,739, filed Jun. 4, 2023.
Haimi-Cohen et al., U.S. Appl. No. 18/328,738, filed Jun. 4, 2023.
Katsir et al., U.S. Appl. No. 18/319,518, filed May 18, 2023.
Haimi-Cohen et al., U.S. Appl. No. 18/105,848, filed Feb. 5, 2023.
Haimi-Cohen et al., U.S. Appl. No. 18/105,847, filed Feb. 5, 2023.
International Application # PCT/IB2024/050483 Search Report dated May 7, 2024.
EP Application # 21832054.7 Search Report dated Mar. 11, 2024.
International Application # PCT/IB2024/054360 Search Report dated Jun. 28, 2024.
JP Application # 2022576351 Office Action dated Jul. 2, 2024.
U.S. Appl. No. 17/902,836 Office Action Jul. 8, 2024.
International Application # PCT/IB2024/054359 Search Report dated Jul. 9, 2024.
AU Application # 2021384028 Office Action Aug. 15, 2024.
EP Application # 24181539.8 Search Report dated Sep. 4, 2024.

* cited by examiner

FIG. 3

DIAGNOSIS OF MEDICAL CONDITIONS USING VOICE RECORDINGS AND AUSCULTATION

CROSS-REFERENCE TO RELATED APPLICATION

This application is a continuation of U.S. patent application Ser. No. 16/807,178, filed Mar. 3, 2020, now U.S. Pat. No. 11,484,211.

FIELD OF THE INVENTION

The present invention relates generally to systems and methods for medical diagnosis, and particularly to detection and assessment of pulmonary edema.

BACKGROUND

Pulmonary edema is a common result of heart failure, in which fluid accumulates within the parenchyma and air spaces of the lungs. It leads to impaired gas exchange and may cause respiratory failure.

Patients with heart failure can be kept in stable condition ("compensated") with appropriate medications for long periods of time. Various unexpected changes, however, may destabilize the patient's condition, resulting in "decompensation." In the beginning of the decompensation process, fluid leaks out of the pulmonary capillaries into the interstitial space around the alveoli. As the fluid pressure in the interstitial spaces increases, the fluid leaks out of the interstitial space into the alveoli, and breathing becomes difficult. It is important to detect and treat decompensation at an early stage, before respiratory distress sets in.

Various methods are known in the art for detecting fluid accumulation in the lungs. For example, PCT International Publication WO 2017/060828, whose disclosure is incorporated herein by reference, describes apparatus in which a processor receives speech of a subject who suffers from a pulmonary condition related to accumulation of excess fluid. The processor identifies, by analyzing the speech, one or more speech-related parameters, assesses, in response to the speech-related parameters, a status of the pulmonary condition, and generates an output indicative of the status of the pulmonary condition.

As another example, Mulligan, et al., described the use of audio response in detecting fluid in the lungs in an article entitled, "Detecting regional lung properties using audio transfer functions of the respiratory system," published in the 2009 *Annual International Conference of the IEEE Engineering in Medicine and Biology Society* (IEEE, 2009). The authors developed an instrument for measuring changes in the distribution of lung fluid the respiratory system. The instrument consists of a speaker that inputs a 0-4 kHz White Gaussian Noise (WGN) signal into a patient's mouth and an array of four electronic stethoscopes, linked via a fully adjustable harness, used to recover signals on the chest surface. The software system for processing the data utilizes the principles of adaptive filtering in order to obtain a transfer function that represents the input—output relationship for the signal as the volume of fluid in the lungs is varied.

SUMMARY

Embodiments of the present invention that are described hereinbelow provide improved methods and apparatus for detection of pulmonary conditions.

There is therefore provided, in accordance with an embodiment of the invention, a method for medical diagnosis, which includes recording voice signals due to sounds spoken by a patient and recording acoustic signals output, simultaneously with the voice signals, by an acoustic transducer in contact with a thorax of the patient. A transfer function is computed between the recorded voice signals and the recorded acoustic signals or between the recorded acoustic signals and the recorded voice signals. The computed transfer function is evaluated in order to assess a medical condition of the patient.

In some embodiments, evaluating the computed transfer function includes evaluating a deviation between the computed transfer function and a baseline transfer function, and detecting a change in the medical condition of the patient responsively to the evaluated deviation. In one embodiment, detecting the change includes detecting an accumulation of a fluid in the thorax of the patient. The method may include administering a treatment to the patient, responsively to detecting the change, so as to reduce an amount of the fluid accumulated in the thorax.

Alternatively or additionally, evaluating the computed transfer function includes assessing an interstitial lung disease in the patient.

In a disclosed embodiment, the method includes administering a treatment to the patient in order to treat the assessed medical condition.

In some embodiments, recording the acoustic signals includes eliminating heart sounds from the acoustic signals output by the acoustic transducer before computing the transfer function. In one embodiment, eliminating the heart sounds includes detecting intervals of occurrence of extraneous sounds, including the heart sounds, in the acoustic signals, and eliminating the intervals from the acoustic signals that are used in computing the transfer function.

Additionally or alternatively, eliminating the heart sounds includes filtering the heart sounds out of the recorded acoustic signals before computing the transfer function. In a disclosed embodiment, recording the acoustic signals includes receiving at least first and second acoustic signals, respectively, from at least first and second acoustic transducers in contact with the thorax, and filtering the heart sounds includes applying a delay in arrival of the heart sounds in the second acoustic signal relative to the first acoustic signal in combining the first and second acoustic signal while filtering out the heart sounds.

Further additionally or alternatively, computing the transfer function includes computing respective spectral components of the recorded voice signals and the recorded acoustic signals at a set of frequencies, and calculating a set of coefficients representing a relation between the respective spectral components. In one embodiment, the coefficients are a representation of a cepstrum.

In some embodiments, computing the transfer function includes calculating a set of coefficients representing a relation between the recorded voice signals and the recorded acoustic signals in terms of an infinite impulse response filter.

Alternatively or additionally, computing the transfer function includes calculating a set of coefficients representing a relation between the recorded voice signals and the recorded acoustic signals in terms of a predictor in a time domain. In one embodiment, calculating the set of coefficients includes applying a prediction error of the relation in computing adaptive filter coefficients relating the recorded voice signals and the recorded acoustic signals.

In a disclosed embodiment, computing the transfer function includes dividing the spoken sounds into phonetic units of multiple different types, and calculating separate, respective transfer functions for the different types of phonetic units.

In some embodiments, computing the transfer function includes calculating a set of time-varying coefficients representing a temporal relation between the recorded voice signals and the recorded acoustic signals. In a disclosed embodiment, calculating the set of time-varying coefficients includes identifying a pitch of the spoken voice signals, and constraining the time-varying coefficients to be periodic, with a period corresponding to the identified pitch.

Additionally or alternatively, computing the transfer function includes calculating a set of coefficients representing a relation between the recorded voice signals and the recorded acoustic signals, and evaluating the deviation includes computing a distance function between the coefficients of the computed transfer function and the baseline transfer function. In one embodiment, computing the distance function includes calculating respective differences between pairs of coefficients, wherein each pair includes a first coefficient in the computed transfer functions and a second, corresponding coefficient in the baseline transfer function, and computing a norm over all the respective differences. Further additionally or alternatively, computing the distance function includes observing differences between transfer functions computed in different health states, and choosing the distance function responsively to the observed differences.

There is also provided, in accordance with an embodiment of the invention, apparatus for medical diagnosis, including a memory, which is configured to store recorded voice signals due to sounds spoken by a patient and recorded acoustic signals output, simultaneously with the voice signals, by an acoustic transducer in contact with a thorax of the patient. A processor is configured to compute a transfer function between the recorded voice signals and the recorded acoustic signals or between the recorded acoustic signals and the recorded voice signals, and to evaluate the computed transfer function in order to assess a medical condition of the patient.

There is additionally provided, in accordance with an embodiment of the invention, a computer software product, including a non-transitory computer-readable medium in which program instructions are stored, which instructions, when read by a computer, cause the computer to receive voice signals due to sounds spoken by a patient and acoustic signals output, simultaneously with the voice signals, by an acoustic transducer in contact with a thorax of the patient, to compute a transfer function between the recorded voice signals and the recorded acoustic signals or between the recorded acoustic signals and the recorded voice signals, and to evaluate the computed transfer function in order to assess a medical condition of the patient.

The present invention will be more fully understood from the following detailed description of the embodiments thereof, taken together with the drawings in which:

DETAILED DESCRIPTION OF EMBODIMENTS

Overview

The initial stages of decompensation in heart failure patients can be asymptomatic. By the time symptoms appear and the patient feels signs of distress, the patient's condition may progress rapidly. In many cases, by the time the patient seeks and receives medical attention and begins treatment, fluid accumulation in the lungs can be severe, requiring hospitalization and lengthy medical intervention. It is therefore desirable that the patient be monitored frequently—even daily—in order to detect initial signs of fluid accumulation in the thorax. The monitoring technique should be simple enough to be administered by the patient or members of the patient's family, but sensitive enough to detect small, subtle changes in fluid levels.

Embodiments of the present invention that are described herein address the need for frequent, convenient monitoring by recording and comparing sounds spoken by the patient to sounds that are transmitted through the patient's thorax to an acoustic transducer in contact with the body surface of the thorax. (Such transducers are used in electronic stethoscopes that are known in the art, and the process of listening to and recording sounds at the body surface is referred to as auscultation.) Fluid accumulation is known to influence both spoken sounds and thoracic sounds, and techniques using each of these types of sounds by itself have been developed for detecting pulmonary edema. In the present embodiments, however, the relation between these two types of sounds in a given patient is monitored in order to provide a much more sensitive indicator of changes in fluid levels.

Specifically, in the disclosed embodiments, the patient or a caregiver affixes one or more acoustic transducers to the patient's thorax at a predefined location or locations. The patient then speaks into a microphone. A recording device, such as a mobile telephone running a suitable application, records voice signals from the microphone (in the form of digitized electrical signals) and simultaneously records the digitized acoustic signals output by the acoustic transducer or transducers. A processor (either in the recording device or in a remote computer) computes a profile of the correspondence between the voice signals and the acoustic signals in terms of a transfer function between the recorded voice signals and the recorded acoustic signals or between the recorded acoustic signals and the recorded voice signals.

The term "transfer function" is used in the present description and in the claims in a sense similar to that used in the field of communications, to mean a functional relation between two time-varying signals. The transfer function may be linear or nonlinear, as illustrated in the embodiments described below. For the purpose of computing the transfer function, one of the signals—either the recorded voice signals or the recorded acoustic signals—is treated as the input signal, while the other is treated as the output signal. (In contrast to actual communication signals, the choice of input and output signals is arbitrary in the present case.) The transfer function is typically expressed in terms of a set of coefficients, which may be computed, based on the "input" and "output" signals, in either the time domain or the frequency domain. Various types of transfer functions, including both time-invariant and time-varying transfer functions, that may be used for this purpose are described below, along with methods for their computation.

The processor examines the transfer function in order to detect a change in the patient's medical condition, and specifically to detect accumulation of fluid in the thorax. In such a case, medical personnel may be prompted to administer a treatment to the patient, for example initiating or increasing the dosage of an appropriate medication, such as a diuretic or beta blocker.

The examination of the transfer function may be patient-independent or patient-specific. Patient-independent examination uses knowledge gathered by inspecting the transfer functions of a large number of people in different health states to determine the characteristics that distinguish transfer functions of healthy people from those of people with certain medical conditions. For example, if the transfer function is expressed in the frequency domain, the distinguishing characteristics may include the ratio between the mean power of the transfer function in two different frequency bands.

In patient-specific examination, the processor evaluates the deviation between the computed transfer function and a baseline transfer function. This baseline can comprise or be derived from one or more transfer functions that were computed for this same patient during a period of good health. Additionally or alternatively, the baseline may be based on samples collected over a larger patient population. Significant deviations can be indicative of a change in the patient's medical condition, and specifically of accumulation of fluid in the thorax.

In some embodiments, a second, "edema" baseline transfer function can be compared to the computed baseline function. This second baseline transfer function may be equal to or derived from a transfer function that was computed for this same patient during a period of pulmonary edema. Additionally or alternatively, the second baseline transfer function may be based on samples collected over a larger patient population, when those patients experienced pulmonary edema. Low deviations from the "edema" baseline may be indicative of a change in the patient's medical condition, and specifically of accumulation of fluid in the thorax. In some cases, the only available baseline may be an "edema" baseline transfer function, for example if monitoring the patient started when the patient was hospitalized due to acute pulmonary edema. In this case, an alert is raised if the deviation from the edema baseline becomes too small. In other cases, both a "stable" baseline transfer function and an "edema" baseline transfer function may be available, and an alert is raised if the deviation from the edema baseline becomes too small and the deviation from the "stable" baseline is too large.

As explained above, embodiments of the present invention are particularly useful in detecting and treating changes in fluid levels due to heart failure. Additionally or alternatively, these techniques may be applied in diagnosing and treating other conditions that can result in pulmonary edema, such as high altitude, adverse drug reaction. For example, if a patient is about to travel to high altitude, or to be treated with a drug with a potential risk of pulmonary edema, a baseline may be obtained before entering the risky condition (i.e., while still at low altitudes, or before taking the drug). The patient can then be monitored using the method described above, at a frequency of checking appropriate for the condition.

In addition to pulmonary edema, there are other conditions that can change the acoustic conductance properties of the lungs, such as interstitial lung disease, in which the alveoli walls get thicker and stiffer. Any such condition affects the transfer function and therefore can be detected using the present methods.

SYSTEM DESCRIPTION

Figure 1:
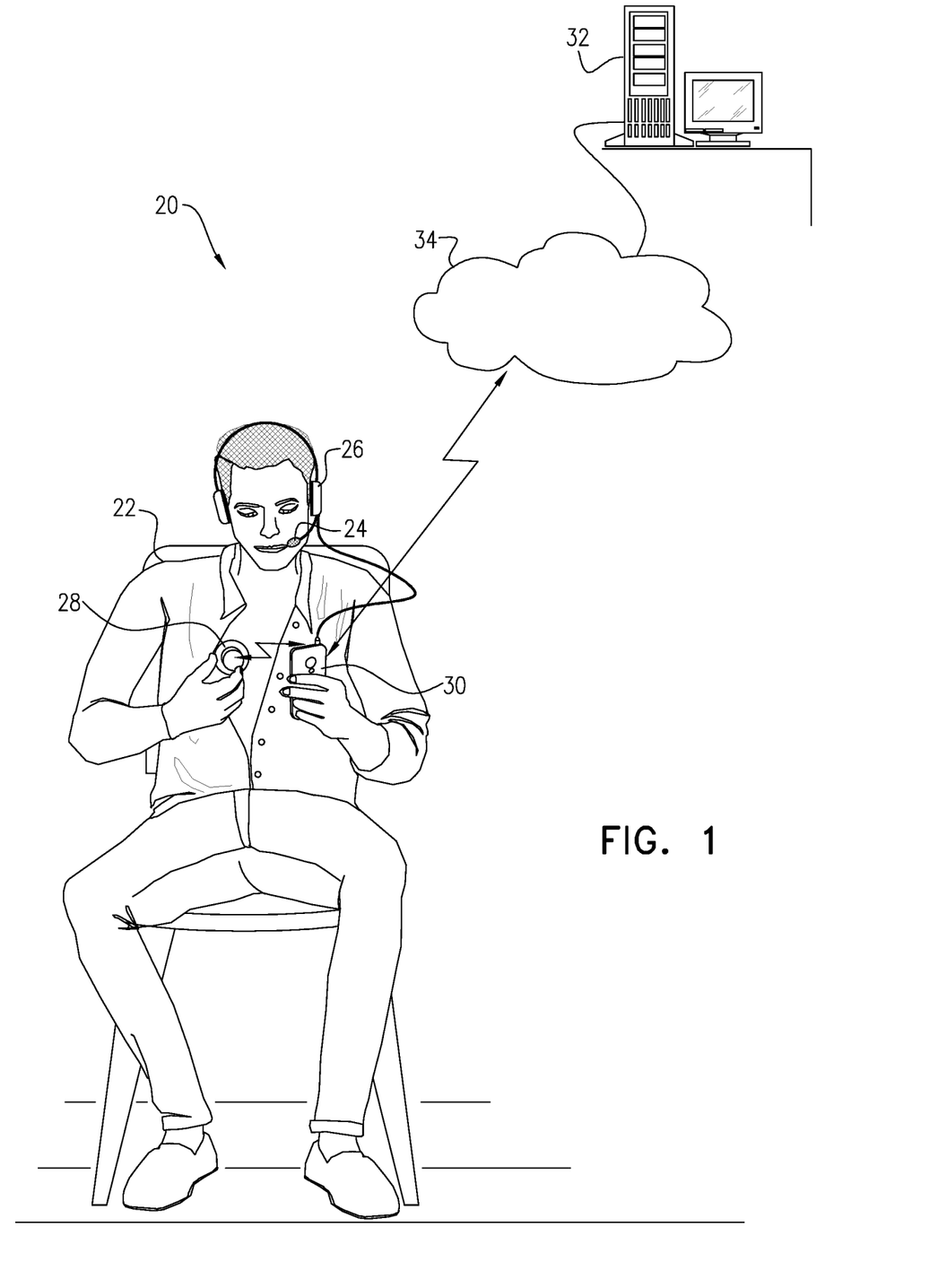
FIG. 1 is a schematic pictorial illustration of a system for detection of pulmonary conditions, in accordance with an embodiment of the invention.
Figure 2:
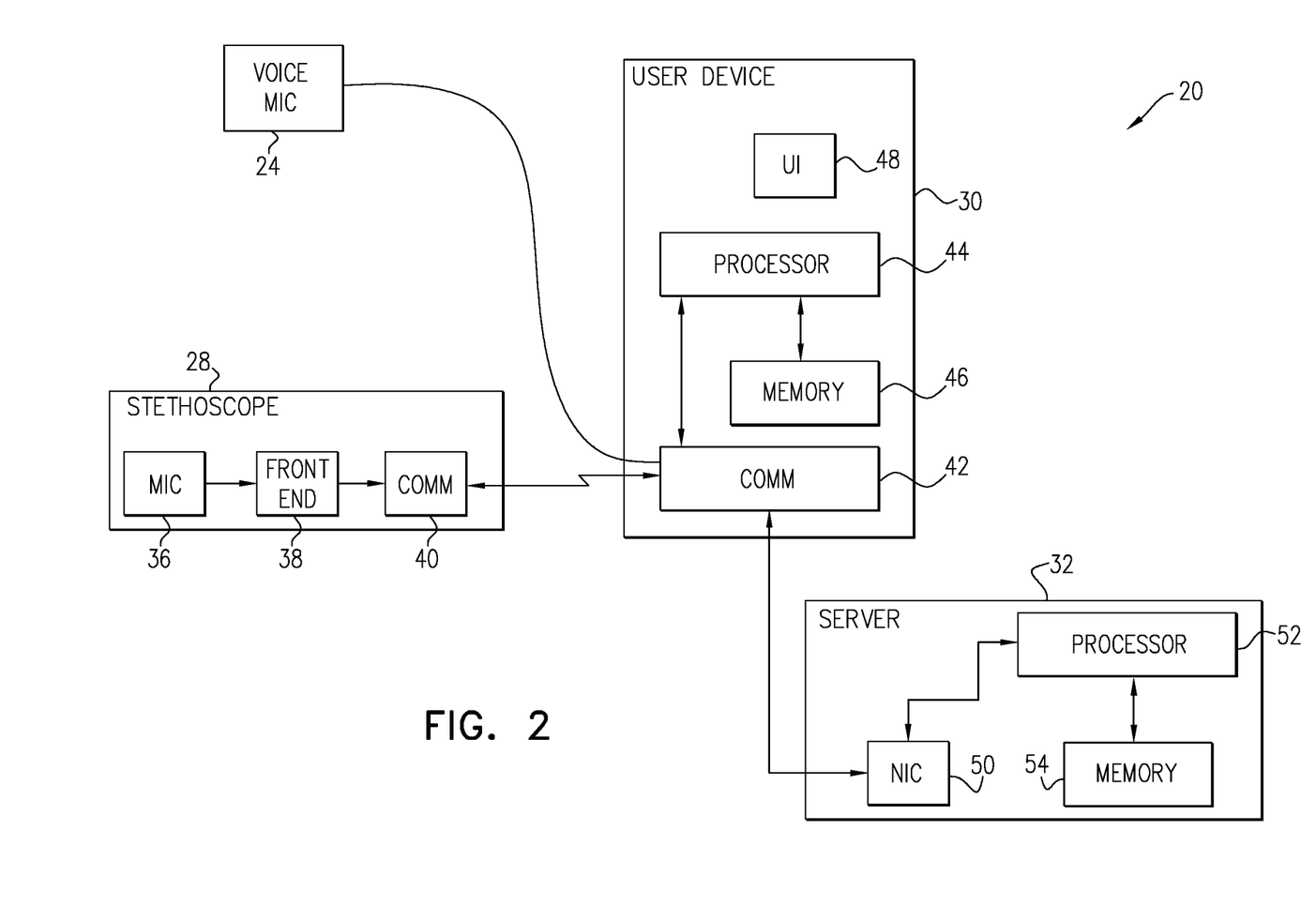
FIG. 2 is a block diagram that schematically shows details of the elements of the system of FIG. 1, in accordance with an embodiment of the invention.

Reference is now made to FIGS. 1 and 2, which schematically illustrate a system 20 for detection of pulmonary conditions, in accordance with an embodiment of the invention. FIG. 1 is a pictorial illustration, while FIG. 2 is a block diagram showing details of the elements of the system.

In the pictured embodiment, a patient 22 utters sounds into a voice microphone 24, such as a microphone that is part of a headset 26, which is connected to a user device 30, such as a smartphone, tablet, or personal computer. The patient may be prompted, for example via the earphones of headset 26 or the screen of device 30, to utter specific sounds or he may speak freely. Microphone 24 may alternatively be built into device 30, or it may be a freestanding unit, which is connected to device 30 by a wired or wireless connection.

An acoustic transducer 28 is placed in contact with the patient's thorax before he begins speaking. Transducer 28 may be contained in an electronic stethoscope, such as a Littmann® Electronic Stethoscope, produced by 3M (Maplewood, Minnesota), which the patient or a caregiver holds in place. Alternatively, transducer 28 may be a special-purpose device, which may be affixed to the thorax using adhesive, a suction cup, or a suitable belt or harness. Although only a single transducer of this sort is shown in the figures, placed on the subject's chest, in alternative embodiments, a transducer or multiple transducers may be placed at different locations around the thorax, such as on the subject's back. Additionally or alternatively, acoustic transducer 28 may be permanently fixed to the body of patient 22, for example as a part of the subcutaneous control unit of a pacemaker or intracardiac defibrillator.

As shown in FIG. 2, acoustic transducer 28 comprises a microphone 36, such as a piezoelectric microphone, which contacts the skin of the chest directly or through a suitable interface. Front end circuits 38 amplify, filter and digitize the acoustic signals output by microphone 36. In an alternative embodiment (not shown in the figures), the same front end circuits 38 also receive and digitize the voice signals from voice microphone 24. A communications interface 40, such as a Bluetooth® wireless interface, transmits the resulting stream of digital samples to user device 30. Alternatively, front end circuits 38 may convey the acoustic signals in analog form over a wired interface to user device 30.

User device 30 comprises a communications interface 42, which receives the voice signals output by microphone 24 and the acoustic signals output by transducer 28 over wired or wireless links. A processor 44 in user device 30 records the signals as data in a memory 46, such as a random access memory (RAM). Typically, the recordings of the signals from microphone 24 and transducer 28 are synchronized with one another. This synchronization may be achieved by synchronizing the sampling circuits that are used in acquiring and digitizing the signals, or possibly by using the same sampling circuit for both of microphones 24 and 36, as noted above. Alternatively, processor 44 may synchronize the recordings on the basis of acoustic events that occur in both the voice signals and the acoustic signals, either as part of the patient's speech or as an artificial added sound, such as clicks generated by an audio speaker in user device 30 at regular intervals. A user interface 48 of user device 30 outputs instructions to the patient or caregiver, for example via headset 26 or on a display screen.

In the present embodiment, processor 44 transmits the recorded signals as data via a network 34, such as the Internet, to a server 32 for further analysis. Alternatively or additionally, processor 44 may perform at least a part of the analysis locally, within user device 30. Server 32 comprises a network interface controller (NIC) 50, which receives and passes the data to a processor 52 and conveys the data to a memory 54 of the server for storage and subsequent analysis. Although FIG. 1 shows only a single patient 22 and user device 30, in practice server 32 will typically communicate with multiple user devices and provide service to multiple patients.

As described in detail hereinbelow, processor 52 computes a transfer function between the recorded voice signals and the recorded acoustic signals or between the recorded acoustic signals and the recorded voice signals. Processor 52 evaluates a deviation between the computed transfer function and a baseline transfer function, and reports the results to patient 22 and/or to a caregiver. Based on this deviation, processor 52 may detect a change in the patient's condition, such as an increased accumulation of fluid in the patient's thorax. In this case, server 32 will typically issue an alert to medical personnel, such as the patient's physician, who may then prescribe a treatment to reduce the fluid accumulation.

Processor 44 and processor 52 typically comprise general-purpose computer processors, which carry out the functions described herein under the control of suitable software. This software may be downloaded to the processors in electronic form, over network 34, for example. Additionally or alternatively, the software may be stored in tangible, non-transitory computer-readable media, such as optical, magnetic, or electronic memory media. Further additionally or alternatively, at least some of the functions of processors 44 and 52 may be performed by a special-purpose digital signal processor or by hardware logic circuits.

METHODS FOR SIGNAL ANALYSIS AND EVALUATION

Figure 3:
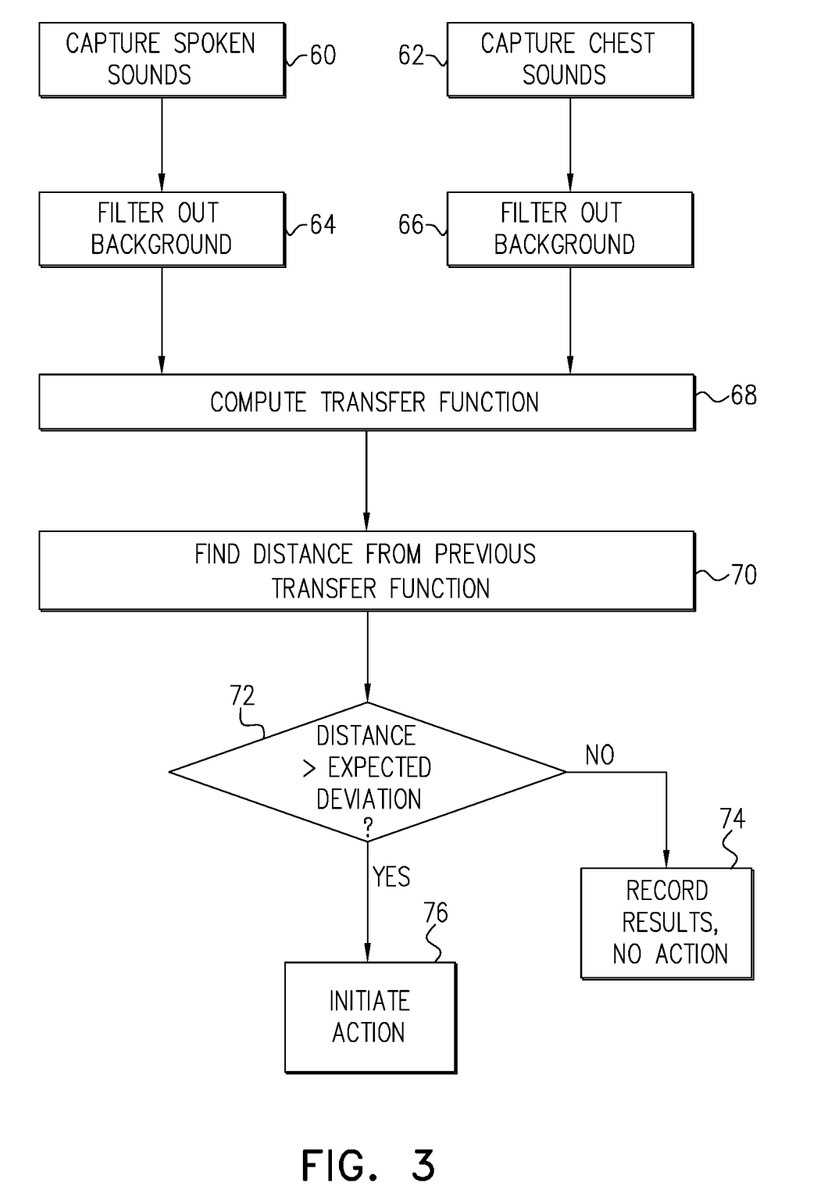
FIG. 3 is a flow chart that schematically illustrates a method for detection of a pulmonary condition, in accordance with an embodiment of the invention.

FIG. 3 is a flow chart that schematically illustrates a method for detection of a pulmonary condition, in accordance with an embodiment of the invention. The method is described here, for the sake of clarity and convenience, with reference to the elements of system 20, as shown in the preceding figures and described above. Alternatively, the principles of the present method may be implemented in substantially any system with the capability of simultaneously recording and then analyzing spoken sounds and thoracic sounds, both for detecting pulmonary edema and for other medical conditions. All such alternative implementations are considered to be within the scope of the present invention.

The method begins with acquisition of input signals: Microphone 24 captures sounds spoken by patient 22 and outputs voice signals, at a speech capture step 60. Simultaneously, acoustic transducer 28 is held in contact with the patient's thorax to capture chest sounds, and outputs corresponding acoustic signals at an auscultation step 62. Processor 44 records the signals, in digital form, in memory 46. As noted earlier, the voice signals and acoustic signals are synchronized either by synchronized sampling at the time of capture or subsequently, for example by processor 44, by aligning acoustic features of the recorded signals.

In the present embodiment, processor 44 transmits the raw, digitized signals to server 32 for further processing. Therefore, the steps that follow in FIG. 4 are described below with reference to the elements of server 32. Alternatively, some or all of these processing steps may be performed locally by processor 44.

Processor 52 stores the data received from user device 30 in memory 54 and filters the data to remove background sounds and other noise. Processor 52 filters the voice signals to remove interference due to background noises, using methods of audio processing that are known in the art, at a speech filtering step 64. Processor 52 filters the acoustic signals from transducer 28 to eliminate chest sounds that are not directly connected to the patient's speech, such as the sounds of heartbeats, peristaltic movements in the digestive system, and wheezing, at an acoustic filtering step 66. For example, at steps 64 and 66, processor 52 may detect extraneous sounds in the voice signals and/or the acoustic signals and may simply ignore time intervals in which the extraneous sounds occurred. Alternatively or additionally, processor 52 may actively suppress the background sounds and noise.

The detection of the extraneous sounds may be done in several ways. In some cases, the unique acoustic properties of the extraneous sound may be used. For example, in the case of heartbeats, the typical periodicity may be used; the period and acoustic characteristics of the heartbeats may be detected during a period of silence, when the patient is not speaking, and then used to detect the heartbeats during speech.

As will be explained below, the transfer function can be represented as a predictor of the chest sound signal using the microphone signal. The prediction error is the difference between the actual chest signal and the predicted value. In some embodiments, the prediction error is computed, and a significant increase in its power, or in its power in specific frequency bands, is indicative of the presence of an extraneous signal.

If multiple acoustic transducers are used, the sound waves emitted from sources in the body arrive at each of the transducers with a slightly different delay and attenuation (which may be different in different frequency bands). These differences in delay and attenuation depend on the location of the sound source. Thus, extraneous sounds that arrive from sources such as the heart or the digestive system can be detected because their relative delays are different from the relative delays of the speech sounds. On this basis, in some embodiments, processor 52 receives the signals from multiple transducers affixed to the patient's body, and uses the relative delays, in order to combine the signals while filtering out the extraneous sounds. In some embodiments with multiple acoustic transducers, beamforming techniques, known from the field of microphone arrays, may be used to suppress the gains of extraneous sounds, which arrive from a different direction than the speech sound.

In one embodiment, for example, processor 52 detects heart sounds in the acoustic signals output by transducer 28 and thus measures the heart rate. On this basis, the processor computes a matched filter, which is matched in the spectral or temporal domain to the spectrum of the heart sounds, and applies the matched filter in suppressing the contribution of the heart sounds to the acoustic signals at step 66.

In another embodiment, for example, processor 52 uses an adaptive filter to predict the acoustic signal caused by the heartbeats in the acoustic signals of previous heartbeats, and subtracts the predicted heartbeat from the recorded signal, thus substantially cancelling the effect of the heartbeat.

Transfer Function Estimation

After filtering the signals, processor 52 computes a transfer function between the recorded voice signals and the recorded acoustic signals, at a correspondence computation step 68. As explained above, the transfer function is conveniently expressed as a transfer function h(t), which predicts one of the signals as a function of the other. In the description that follows, it will be assumed that the voice signal output by microphone 24, $x_M(t)$, predicts the acoustic signal output by transducer 28, $x_S(t)$, according to the relation $x_S=h*x_M$. For the purpose of computation, the acoustic signal may, if necessary, be arbitrarily delayed by a short period, for example a few milliseconds. Alternatively, the procedures described below may be applied, mutatis mutandis, in computing a transfer function that predicts $x_M$ as a function of $x_S$.

In some embodiments, processor 52 computes the transfer function $H(\omega)$ in the spectral domain. In this case, the transfer function can be calculated as a set of coefficients representing the spectral components of the acoustic signal $X_S$ (W) at a set of frequencies $\{\omega\}$ in terms of those of the sound signal $X_M(\omega)$. Since the signals are sampled at a certain sampling frequency, the frequency components of the signals and transfer function can be conveniently represented as points on a unit circle $H(e^{i\omega}), X_M(e^{i\omega}), X_S(e^{i\omega})$, with $|\omega| \leq \pi$, wherein w is the normalized frequency (equal to $2\pi$ times the actual frequency divided by the sampling frequency). The transfer function coefficient for each frequency component w is then given by:

$$H(e^{i\omega}) = \frac{X_S(e^{i\omega})}{X_M(e^{i\omega})} \quad (1)$$

Typically, the frequency components of $X_S$ and $X_M$ are computed at N discrete frequencies by means of a suitable transform function, such as a discrete Fourier transform (DFT). The quotient of equation (1) gives the coefficients of H at N equally-spaced points on the unit circle, defined by $e^{2\pi i n/N}$, $n=0, \ldots, N-1$.

Alternatively, H may be represented more compactly in terms of a cepstrum, for example in the form of cepstral coefficients. The cepstral coefficients $c_k$, $-\infty < k < \infty$, are the Fourier coefficients of $\log(H(e^{i\omega}))$. Since the signals $x_M$ and $x_S$ are real-valued, the sequence of cepstral coefficients is conjugate symmetric, i.e., $c_k = \overline{c_{-k}}$, and hence:

$$\log(H(e^{i\omega})) = \Sigma_{k=-\infty}^{\infty} c_k e^{i\omega k} = c_0 + 2 \Sigma_{k=1}^{\infty} [\text{Re}\{c_k\} \cos \omega k + i \text{Im}\{c_k\} \sin \omega k] \quad (2)$$

The cepstral coefficients can be computed using techniques that are known in the art, in which equation (2) is approximated using a small, finite number p+1 of cepstral coefficients:

$$\log(H(e^{i\omega})) \approx \Sigma_{k=-p}^{p} c_k e^{i\omega k} = c_0 + 2 \Sigma_{k=1}^{p} [\text{Re}\{c_k\} \cos \omega k + i \text{Im}\{c_k\} \sin \omega k] \quad (3)$$

The coefficients $[c_0, \ldots, c_p]$ thus represent the frequency response of the transfer function. Alternatively, the transfer function can be represented in terms of the first p+1 real cepstral coefficients, which are the cepstral representation of $\log |H(e^{i\omega})|$.

In an alternative embodiment, processor 52 calculates the transfer function in terms of a set of coefficients representing a relation between the recorded voice signals and the recorded acoustic signals as an infinite impulse response filter:

$$H(e^{i\omega}) = \frac{\Sigma_{l=0}^{q} b_l e^{i\omega l}}{1 + \Sigma_{k=1}^{p} a_k e^{i\omega k}} \quad (4)$$

Alternatively, this transfer function may be represented in the time domain as:

$$\hat{x}_S[n] = \Sigma_{l=0}^{q} b_l x_M[n-l] - \Sigma_{k=1}^{p} a_k x_S[n-k] \quad (5)$$

Here $x_M[n]$, $x_S[n]$ are the time domain samples, at time n, of the signals output by microphone 24 and transducer 28, respectively, and $\hat{x}_S[n]$ is the predictor of the transducer signal at time n. The coefficients $a_1, \ldots, a_p, b_0, \ldots, b_q$ define the frequency response in equation (4), and they can be estimated, for example, by minimizing the mean square prediction error, $\Sigma_{n=q}^{N-1} |\hat{x}_S[n] - x_S[n]|^2$, over the available data points, $x_M[n]$, $x_S[n]$, $n=0, \ldots, N-1$.

The above equations assume implicitly that a single, time-invariant transfer function is computed between the voice signals recorded by microphone 24 and the acoustic signals from transducer 28. Some embodiments of the present invention, however, do not rely on this assumption.

From a physical standpoint, the process of speech sound generation consists of three main stages: excitation, modulation and propagation. The excitation happens when the air flow out of the lungs is constricted or intermittently blocked, which creates the excitation signal. Excitation may be caused by the vocal cords intermittently blocking the air flow, or by higher articulating organs, such as the tongue and lips, blocking or constricting the air flow at different points in the vocal tract. The excitation signal is modulated by reverberating inside the vocal tract and possibly also in the tracheo-bronchial space. Finally, the modulated signal propagates out, both through the nose and mouth, where it is received by microphone 24, and through the lungs and the chest walls, where it is received by transducer 28. The transfer function between the microphone and the transducer varies according to the location of the excitation, and therefore, it may be different for different phonemes.

The term "phonemes" generally refers to distinct phonetic components of speech. To clarify our terminology, "voice" denotes any sound generated in the subject's respiratory system, which can be captured by a microphone placed in front of the subject. "Speech" is voice that represents specific syllables, words or sentences. Our paradigm is based on having the subject speak, that is, generate speech, either of a prescribed text or freely chosen by the subject. However, the recorded voice may include, in addition to the speech, various additional, often involuntary, non-speech sounds such as wheezing, coughing, yawning, interjection sounds ("umm", "hmm"), and sighs. Such sounds are generally captured by transducer 28 and result in characteristic transfer functions, according to the location of excitation that generates them. In embodiments of the present invention, these non-speech sounds, to the extent that they occur, can be treated as additional phonetic units, which have their characteristic transfer functions.

Consequently, in one embodiment, processor 52 divides the spoken sounds into phonetic units of multiple different types, and calculates separate, respective transfer functions for the different types of phonetic units. For example, processor 52 may compute phoneme-specific transfer functions. For this purpose, processor 52 can identify phoneme boundaries by using a reference speech signal of the same verbal content, in which the phoneme boundaries are known. Such a reference speech signal may be based on speech recorded from patient 22 at an earlier time, or on speech by another person or on synthesized speech. The signals from microphone 24 and transducer 28 are non-linearly aligned with the reference signal (for example, using dynamic time warping), and the phoneme boundaries are then mapped back from the reference signal to the current signals. Methods for identifying and aligning phoneme boundaries are described further in U.S. patent application Ser. No. 16/299,178, filed Mar. 12, 2019, whose disclosure is incorporated herein by reference.

After separating the input signals into phonemes, processor 52 then computes the transfer function individually for each phoneme or for collections of phonemes of similar types. For example, processor 52 may group together phonemes that are generated by excitation at the same place in the vocal tract. Such grouping enables processor 52 to reliably estimate the transfer function over a relatively short recording time. The processor can then compute one transfer function for all the phonemes in the same group, such as all glottal consonants and all dental consonants. In any case, the correspondence between the signals from microphone 24 and transducer 28 is defined by the multiple phoneme-specific or phoneme-type-specific transfer functions. Alternatively, processor 52 may compute transfer functions for other sorts of phonetic units, such as diphones or triphones.

In the embodiments described above, processor 52 computes the transfer function between the signals from microphone 24 and transducer 28 in terms of a linear, time-invariant set of coefficients (in either the time or frequency domain). This sort of computation can be carried out efficiently and results in a compact numerical representation of the transfer function.

In an alternative embodiment, however, at least some of the coefficients of the transfer function that processor 52 computes are time-varying, representing a temporal relation between the voice signals recorded by microphone 24 and the acoustic signals recorded by transducer 28. This sort of time-varying representation is useful in analyzing voiced sounds, and in particular vowels. In these sounds the vocal cords are active, going through periodic cycles of closing and opening at a rate of more than a hundred times per second. When the vocal cords are open, the tracheo-bronchial tree and vocal tract are one contiguous space, and sounds reverberate between them. On the other hand, when the vocal cords are closed, the sub-glottal space (the tracheo-bronchial tree) and the supra-glottal space (the vocal tract above the vocal cords) are disconnected, and sound cannot reverberate between them. Therefore, in voiced sounds, the transfer function is not time-invariant.

In voiced sounds, the excitation to the supra-glottal space is periodic, with a period corresponding to one cycle of the vocal cords closing and opening again (corresponding to the "fundamental frequency" of the sound). Therefore the excitation can be modeled as a train of uniform pulses, with an interval equal to the period of vibration of the vocal cords between successive pulses. (Any spectral shaping caused by the vocal cords is effectively lumped into the modulation in the vocal tract). The excitation of the sub-glottal space is also caused by the vocal tract, and hence it can be modeled by the same train of uniform pulses. Since in the frequency domain, the voice signals and the acoustic signals are products of the excitation signal by the supra-glottal and sub-glottal transfer functions, respectively, their spectra also consist of pulses, at the same frequencies as the pulses of the excitation and at amplitudes that are proportional to the respective transfer functions.

Thus, in one embodiment, processor 52 applies this model in estimating the spectral envelopes of the voice signals and the acoustic signals, and thus estimates the transfer functions of the vocal tract, $H_{VT}(e^{i\omega})$, and the tracheo-bronchial tree (including the lung walls) $H_{TB}(e^{i\omega})$. The transfer function of the entire system is then given by:

$$H(e^{i\omega}) = \frac{H_{TB}(e^{i\omega})}{H_{VT}(e^{i\omega})} \tag{6}$$

Processor 52 may compute the spectral envelopes $H_{VT}(e^{i\omega})$ and $H_{TB}(e^{i\omega})$ using methods from the field of in speech recognition, such as computing the cepstrum of each of the signals $X_M(e^{i\omega})$, $X_S(e^{i\omega})$, respectively, by linear predictive coding (LPC), and deriving the spectral envelopes using equation (3) above. Effectively, by considering only the spectral envelope, processor 52 obtains a time-invariant approximation.

The temporal variation of the voiced sounds occurs at a frequency that is a function of the pitch, i.e., the frequency of vibration of the vocal cords. Therefore, in some embodiments, processor 52 identifies the pitch of the spoken sounds, and computes time-varying coefficients of the transfer function between the signals from microphone 24 and transducer 28 while constraining the time-variation to be periodic, with a period corresponding to the pitch. For this purpose, equation (5) may be recast as follows:

$$\hat{x}_S[n] = \Sigma_{l=0}^{q} b_l[n] x_M[n-l] - \Sigma_{k=1}^{p} a_k[n] \hat{x}_S[n-k] \tag{7}$$

The time-varying coefficients $b_l[n]$, $0 \leq l \leq q$, and $a_k[n]$, $0 \leq k \leq p$ are assumed to be periodic in n, with a period T given by the pitch frequency, meaning that T is equal to the duration of a cycle of opening and closing of the vocal cords. The pitch can be found using voice analysis techniques that are known in the art. Processor 52 computes the time-varying coefficient values $b_l[n]$ and $a_k[n]$, for example, by minimizing the mean square prediction error of the transfer function, i.e., minimizing the mean square value of $\hat{x}_S - x_S$.

The method explained above requires the estimation of a relatively large number of coefficients, especially in low-pitched male voices. Reliable determination of that many coefficients may requires a large number of repetitions of specific voiced phonemes, which may be difficult to obtain in routine medical monitoring. To mitigate this difficulty, the coefficients may be expressed as parametric functions representing their time-varying behavior during the vocal cord cycle:

$$b_l[n] = B_l\left(\frac{n}{T}\right), 0 \leq n < T, 0 \leq l \leq q \tag{8}$$

$$a_k[n] = A_k\left(\frac{n}{T}\right), 0 \leq n < T, 0 \leq k \leq p$$

Processor 52 estimates the parametric functions $B_l(v)$, $0 \leq l \leq q$ and $A_k(v)$, $0 \leq k \leq p$, with $0 \leq v < 1$, by minimizing the mean square prediction error as explained above.

For example, assuming that $0 < D < 1$ is the fraction of the time during a vocal cord cycle during which the cords are open, the parametric functions can be expressed in the following manner:

$$B_l(v) = \begin{cases} B_l^0 & 0 \leq v < D \\ B_l^1 & D \leq v < 1 \end{cases} 0 \leq l \leq q \tag{9}$$

$$A_k(v) = \begin{cases} A_k^0 & 0 \leq v < D \\ A_k^1 & D \leq v < 1 \end{cases} 0 \leq k \leq p \tag{10}$$

Here $B_l^0$, $0 \leq l \leq q$ and $A_k^0$, $0 \leq k \leq p$ are the transfer function parameters when the vocal cords are open, and $B_l^1, 0 \leq l \leq q$ and $A_k^1$, $0 \leq k \leq p$ are the transfer function parameters when the vocal cords are closed. In this way the number of parameters that processor 52 is required to estimate is $3(q+p)+1$.

Alternatively, processor 52 may use more elaborate forms of these parametric functions, which can more accurately represent the transfer function in the transition between open and closed states of the vocal cords. For example, $B_l(v)$, $0 \leq l \leq q$ and $A_k(v)$, $0 \leq k \leq p$ may be polynomials or rational functions (ratios of polynomials) of a fixed degree.

In another embodiment, processor 52 applies an adaptive filtering approach in deriving the transfer function. The microphone signal $x_M[n]$ is fed into a time-varying filter, which produces a predictor $\hat{x}_S[n]$ of the transducers signal $x_S[n]$. The prediction error, $\hat{x}_S[n]-x_S[n]$, is computed in each frame and is used to correct the filter and compute the time-varying filter coefficients. The filter may be of the form of equation (7) (but without the constraint that the coefficients be periodic in n). Such an adaptive filter is called an infinite impulse response (IIR) adaptive filter. If p=0, the predictor has the form of a finite impulse response (FIR) adaptive filter:

$$\hat{x}_S[n] = \Sigma_{l=0}^{q} b_l[n] x_M[n-l] \qquad (11)$$

The coefficients of the adaptive filter can be adjusted based on the prediction error using methods that are known in the art.

Using this adaptive filtering approach, processor 52 derives at each sample of the patient's speech a set of adaptive filter coefficients for that sample. Processor 52 may use this sequence of filter coefficients itself to characterize the transfer function. Alternatively, it may be preferable to trim the amount of data that must be saved. For example, processor 52 may keep only every T-th set of filter coefficients, wherein T is a predetermined number (for example, T=100). As another alternative, processor 52 may keep a certain number of filter coefficient sets per phoneme, for example three: one at the beginning of the phoneme, one in the middle and one at the end.

Distance Computation

Returning now to FIG. 3, after computing the transfer functions between the signals from microphone 24 and transducer 28 (using any of the above techniques, or other techniques that are known in the art), processor 52 evaluates the deviation between the computed transfer function and a baseline transfer function, at a distance computation step 70. The "distance" in this context is a numerical value, which is computed over the coefficients of the current and baseline transfer functions and quantifies the difference between them. Any suitable sort of distance measure may be used at step 70; and the distance need not be Euclidean or even symmetrical under reversal of its arguments. Processor 52 compares the distance to a predefined threshold, at a distance evaluation step 72.

As noted earlier, the baseline transfer function that is used as a reference in step 70 may be derived from earlier measurements made on patient 22 or measurements derived from a larger population. In some embodiments, processor 52 computes distances from a baseline comprising two or more reference functions. For example, processor 52 may compute a vector of distances from a set of reference transfer functions, and may then choose the minimum or mean of the distances for evaluation at step 72. Alternatively, processor 52 may combine the reference transfer functions, for example by averaging the coefficients, and may then compute the distance from the current transfer function to the average function.

In one embodiment, these two approaches are combined: The reference transfer functions are clustered based on similarity (meaning that the distances between the transfer functions in the same cluster are small), using k-means clustering, for example. Processor 52 then synthesizes a representative transfer function for each cluster. Processor 52 computes distances between the current transfer function and the representative transfer functions of the different clusters, and then computes a final distance based on these cluster distances.

The definition of the distance between a tested and a reference transfer function depends on the form of the transfer function. For example, assuming $f_T = H_T(e^{i\omega})$ and $f_R = H_R(e^{i\omega})$ to be the current and reference transfer functions, respectively, with $|\omega| \leq \pi$ as defined above in equation (1), the distance d between these transfer functions can be written as follows:

$$d(f_T, f_R) = F(\int_{-\pi}^{\pi} G(H_T(e^{i\omega}), H_R(e^{i\omega}), \omega) d\omega) \qquad (12)$$

Here $G(t,r,\omega)$ defines a distance between a tested frequency response value t and a reference frequency response value r at the frequency $\omega$, and F is a monotonically-increasing function.

In some embodiments, processor 52 need not explicitly calculate the frequency-domain transfer functions $H_T(e^{i\omega})$ and $H_R(e^{i\omega})$ in order to compute the distance at step 70. Rather, because these transfer functions can be expressed in terms of the time-domain impulse response or the cepstral coefficients, as explained above, equation (12) may be expressed and evaluated, exactly or approximately, in terms of operations over sequences of values, such as autocorrelation, cepstral coefficients, or impulse response, which correspond to the transfer functions.

In some embodiments, processor 52 evaluates the distance by calculating respective differences between pairs of coefficients in the current and baseline transfer functions, and then computes a norm over all the respective differences. For example, in one embodiment, the distance $G(t,r,\omega) = W(e^{i\omega})| \log(t) - \log(r)|^p$, wherein p>0 is a constant and $W(e^{i\omega})$ is a weighting function that can give different weights to different frequencies, and $F(u) = u^{1/p}$. In this case, equation (11) has the form of a weighted $L^p$ norm:

$$d(f_T, f_R) = (\int_{-\pi}^{\pi} W(e^{i\omega})| \qquad \log(H_T(e^{i\omega})) - \log (H_R(e^{i\omega}))|^p d\omega)^{1/p} \qquad (13)$$

In the limit, as $p \to \infty$, equation (12) becomes the weighted La' norm, which is simply the supremum of the difference:

$$d(f_T, f_R) = \sup_{|\omega| \leq \pi} (W(e^{i\omega})| \log(H_T(e^{i\omega})) - \log(H_R(e^{i\omega}))|) \qquad (14)$$

As another example, setting W $(e^{i\omega})=1$ and p=2, the distance is reduced to the root-mean-square (RMS) of the difference between the current and baseline log spectra.

Alternatively, the logarithm in equation (13) may be replaced by other monotonically non-decreasing functions, and other values of p and W $(e^{i\omega})$ may be used.

Other embodiments use statistical maximal likelihood approaches, such as the Itakura-Saito distortion, which is obtained by setting:

$$G(t, r, \omega) = \frac{r}{t} - \log \frac{r}{t} - 1 \qquad (15)$$

Further alternatively or additionally, the distance function $G(t,r,\omega)$ may be chosen on the basis of empirical data, based on observing actual transfer functions of a particular patient or many patients in different health states. For example, when research shows that a health deterioration related to a specific disease is manifested by an increase in $\log|H_T(e^{i\omega})|$ for w in a particular frequency range $\Omega$, and the baseline transfer function corresponds to a healthy, stable condition of the patient, the distance may be defined accordingly as follows:

$$G(t, r, \omega) = \begin{cases} \log|t| - \log|r| & \text{if } |t| > |r| \text{ and } \omega \in \Omega \\ 0 & \text{otherwise} \end{cases} \quad (16)$$

As another example, when time-varying transfer function coefficients are used, as in equations (7) and (8), and v=n/T, 0≤n<T, then for each value of 0≤v<1, equation (7) defines a time-varying transfer function:

$$H(e^{i\omega}, v) = \frac{\sum_{l=0}^{q} B_l(v)e^{i\omega}}{1 + \sum_{k=1}^{p} A_k(v)e^{i\omega}} \quad (17)$$

The distance between the current and reference time-varying transfer functions can be defined as the average of the distances between $H_T(e^{i\omega},v)$ and $H_R(e^{i\omega},v)$ for matching values of v:

$$d(f_T, f_R) = \int_0^1 F(\int_{-\pi}^{\pi} G(H_T(e^{i\omega},v), H_R(e^{i\omega},v), \omega) d\omega) dv \quad (18)$$

Finally, in embodiments in which each transfer function comprises multiple phoneme-specific transfer functions, processor 52 computes the distance between each pair of corresponding phoneme-specific components of the current and baseline transfer functions separately, using one of the techniques described above. The result is a set of phoneme-specific distances. Processor 52 applies a scoring procedure to these phoneme-specific distances in order to find a final distance value. For example, the scoring procedure may compute a weighted average of the phoneme-specific distances, in which phonemes that are more sensitive to health changes (based on empirical data) get a higher weight.

In another embodiment the scoring procedure uses rank-order statistics instead of averaging. The phoneme-specific distances are weighted according to sensitivity to health change and then sorted into a sequence in an increasing order. Processor 52 selects the value that appears in a specific place in this sequence (for example, the median value) as the distance value.

Whichever of the above distance measures is used, when processor 52 finds at step 72 that the distance between the current and baseline transfer functions is less than an expected maximal deviation, the processor 52 records the measurement results, but does not generally initiate any further action, at a termination step 74. (Server 32 may notify the patient or caregiver that there has been no change in the patient's condition, or possibly even that the patient's condition has improved.) When the distance exceeds the expected maximal deviation, however, server 32 will initiate an action, at an action initiation step 76. The action may comprise issuing an alert, for example in the form of a message to the patient's caregiver, such as the patient's physician. The alert typically indicates that fluid accumulation in the patient's thorax has increased and prompts the caregiver to administer a treatment, such as administering or changing a dosage of a medication in order to reduce the fluid accumulation.

Alternatively, server 32 may not actively push an alert, but may merely present (for example, on a display, or in response to a query) an indicator of the subject's condition, such as the level of pulmonary edema. The indicator may comprise, for example, a number based on the distance between transfer functions, which represents the estimated level of pulmonary edema, assuming that the correlation between the distance between transfer functions and pulmonary edema has been learned from previous observations of this subject or other subjects. A physician may consult this indicator, along with other medical information, in diagnosis and determining treatments.

In some embodiments, administering and changing dosage of medications is performed automatically, by controlling a drug delivery device without requiring a human caregiver in the loop. In such cases, step 76 may include changing a medication level, with or without issuance of an alert (or the alert may indicate that the medication level has been changed).

In some cases, for example in a hospital or other clinic setting, the distance evaluation at step 72 may indicate an improvement in the subject's condition, rather than deterioration. In this case, the action initiated at step 76 may indicate that the subject may be moved out of intensive care, or released from the hospital.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for medical diagnosis, comprising:
    recording voice signals due to sounds spoken by a patient and propagating out through a nose and mouth of the patient into a voice microphone;
    recording acoustic signals output, simultaneously with the voice signals, by an acoustic transducer in contact with a thorax of the patient;
    computing a transfer function between the recorded voice signals and the recorded acoustic signals or between the recorded acoustic signals and the recorded voice signals;
    evaluating the computed transfer function in order to assess a medical condition of the patient,
    wherein computing the transfer function comprises dividing the spoken sounds into phonetic units of multiple different types, and calculating separate, respective transfer functions for the different types of phonetic units; and
    administering a treatment to the patient in order to treat the assessed medical condition.

2. The method according to claim 1, wherein evaluating the computed transfer function comprises:
    evaluating a deviation between the computed transfer function and a baseline transfer function; and
    detecting a change in the medical condition of the patient responsively to the evaluated deviation.

3. The method according to claim 1, the computed transfer function comprises assessing an interstitial lung disease in the patient.

4. The method according to claim 1, wherein recording the acoustic signals comprises eliminating heart sounds from the acoustic signals output by the acoustic transducer before computing the transfer function.

5. The method according to claim 4, wherein eliminating the heart sounds intervals of occurrence of extraneous sounds, including the heart sounds, in the acoustic signals, and eliminating the intervals from the acoustic signals that are used in computing the transfer function.

6. The method according to claim 4, wherein eliminating the heart sounds comprises filtering the heart sounds out of the recorded acoustic signals before computing the transfer function.

7. The method according to claim 6, wherein recording the acoustic signals comprises receiving at least first and second acoustic signals, respectively, from at least first and second acoustic transducers in contact with the thorax, and wherein filtering the heart sounds comprises applying a delay in arrival of the heart sounds in the second acoustic signal relative to the first acoustic signal in combining the first and second acoustic signal while filtering out the heart sounds.

8. The method according to claim 1, wherein computing the transfer function comprises computing respective spectral components of the recorded voice signals and the recorded acoustic signals at a set of frequencies, and calculating a set of coefficients representing a relation between the respective spectral components.

9. The method according to claim 8, wherein the coefficients are a representation of a cepstrum.

10. The method according to claim 1, wherein computing the transfer function comprises calculating a set of coefficients representing a relation between the recorded voice signals and the recorded acoustic signals in terms of an infinite impulse response filter.

11. The method according to claim 1, wherein computing the transfer function comprises calculating a set of coefficients representing a relation between the recorded voice signals and the recorded acoustic signals in terms of a predictor in a time domain.

12. The method according to claim 11, wherein calculating the set of coefficients comprises applying a prediction error of the relation in computing adaptive filter coefficients relating the recorded voice signals and the recorded acoustic signals.

13. The method according to claim 1, wherein computing the transfer function comprises calculating a set of time-varying coefficients representing a temporal relation between the recorded voice signals and the recorded acoustic signals.

14. The method according to claim 13, wherein calculating the set of time-varying coefficients comprises identifying a pitch of the spoken voice signals, and constraining the time-varying coefficients to be periodic, with a period corresponding to the identified pitch.

15. The method according to claim 2, wherein computing the transfer function comprises calculating a set of coefficients representing a relation between the recorded voice signals and the recorded acoustic signals, and wherein evaluating the deviation comprises computing a distance function between the coefficients of the computed transfer function and the baseline transfer function.

16. The method according to claim 15, wherein computing the distance function comprises calculating respective differences between pairs of coefficients, wherein each pair comprises a first coefficient in the computed transfer function and a second, corresponding coefficient in the baseline transfer function, and computing a norm over all the respective differences.

17. The method according to claim 15, wherein computing the distance function comprises observing differences between transfer functions computed in different health states, and choosing the distance function responsively to the observed differences.

18. Apparatus for medical diagnosis, comprising:
a memory, which is configured to store recorded voice signals due to sounds spoken by a patient and propagating out through a nose and mouth of the patient into a voice microphone and recorded acoustic signals output, simultaneously with the voice signals, by an acoustic transducer in contact with a thorax of the patient; and
a processor, which is configured to compute a transfer function between the recorded voice signals and the recorded acoustic signals or between the recorded acoustic signals and the recorded voice signals, and to use diagnostic information extracted from the computed transfer function to assess a medical condition of the patient,
wherein the processor is configured to divide the spoken sounds into phonetic units of multiple different types, and to calculate separate, respective transfer functions for the different types of phonetic units, and
wherein a treatment is administered to the patient in order to treat the assessed medical condition.

19. The apparatus according to claim 18, wherein the processor is configured to evaluate a deviation between the computed transfer function and a baseline transfer function, and to detect a change in the medical condition of the patient responsively to the evaluated deviation.

20. The apparatus according to claim 18, wherein the processor is configured to assess an interstitial lung disease in the patient responsively to the computed transfer function.

21. The apparatus according to claim 18, wherein the processor is configured to eliminate heart sounds from the acoustic signals output by the acoustic transducer before computing the transfer function.

22. The apparatus according to claim 21, wherein the processor is configured to detect intervals of occurrence of extraneous sounds, including the heart sounds in the acoustic signals output by the acoustic transducer, and to eliminate the intervals from the acoustic signals that are used in computing the transfer function.

23. The apparatus according to claim 21, wherein the processor is configured to filter the heart sounds out of the recorded acoustic signals before computing the transfer function.

24. The apparatus according to claim 23, wherein the memory is configured to receive and store at least first and second acoustic signals, respectively, from at least first and second acoustic transducers in contact with the thorax, and wherein the processor is configured to apply a delay in arrival of the heart sounds in the second acoustic signal relative to the first acoustic signal in combining the first and second acoustic signal while filtering out the heart sounds.

25. The apparatus according to claim 18, wherein the processor is configured to compute respective spectral components of the recorded voice signals and the recorded acoustic signals at a set of frequencies, and to calculate a set of coefficients of the transfer function representing a relation between the respective spectral components.

26. The apparatus according to claim 25, wherein the coefficients are a representation of a cepstrum.

27. The apparatus according to claim 18, wherein the processor is configured to compute a set of coefficients of the transfer function representing a relation between the recorded voice signals and the recorded acoustic signals in terms of an infinite impulse response filter.

28. The apparatus according to claim 18, wherein the processor is configured to compute a set of coefficients of the transfer function representing a relation between the recorded voice signals and the recorded acoustic signals in terms of a predictor in a time domain.

29. The apparatus according to claim 28, wherein the processor is configured to apply a prediction error of the relation in computing adaptive filter coefficients relating the recorded voice signals and the recorded acoustic signals.

30. The apparatus according to claim 18, wherein the processor is configured to compute a set of time-varying coefficients of the transfer function, representing a temporal relation between the recorded voice signals and the recorded acoustic signals.

31. The apparatus according to claim 30, wherein the processor is configured to identify a pitch of the spoken voice signals, and to constrain the time-varying coefficients to be periodic, with a period corresponding to the identified pitch.

32. The apparatus according to claim 19, wherein the processor is configured to compute a set of coefficients of the transfer function representing a relation between the recorded voice signals and the recorded acoustic signals, and to evaluate the deviation by computing a distance function between the coefficients of the computed transfer function and the baseline transfer function.

33. The apparatus according to claim 32, wherein the processor is configured to compute the distance function by calculating respective differences between pairs of coefficients, wherein each pair comprises a first coefficient in the computed transfer functions and a second, corresponding coefficient in the baseline transfer function, and computing a norm over all the respective differences.

34. The apparatus according to claim 32, wherein the processor is configured to compute the distance function responsively to differences observed between transfer functions computed in different health states.

35. A computer software product, comprising a non-transitory computer-readable medium in which program instructions are stored, which instructions, when read by a computer, cause the computer to receive voice signals due to sounds spoken by a patient and propagating out through a nose and mouth of the patient into a voice microphone and acoustic signals output, simultaneously with the voice signals, by an acoustic transducer in contact with a thorax of the patient, to compute a transfer function between the recorded voice signals and the recorded acoustic signals or between the recorded acoustic signals and the recorded voice signals, and to use diagnostic information extracted from the computed transfer function to assess a medical condition of the patient, wherein the instructions cause the computer to divide the spoken sounds into phonetic units of multiple different types, and to calculate separate, respective transfer functions for the different types of phonetic units, and wherein a treatment is administered to the patient in order to treat the assessed medical condition.

* * * * *